United States Patent
Huhtinen et al.

(10) Patent No.: US 8,309,591 B2
(45) Date of Patent: Nov. 13, 2012

(54) TRANSMUCOSAL VETERINARY COMPOSITION COMPRISING DETOMIDINE

(75) Inventors: Mirja Huhtinen, Ilmarinen (FI); Piritta Koistinen, Turku (FI); Lasse Leino, Merimasku (FI); Maria Rantala, Paimio (FI); Helena Kaukinen, Paimio (FI); Kaija Af Ursin, Turku (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 12/953,691

(22) Filed: Nov. 24, 2010

(65) Prior Publication Data

US 2011/0071203 A1    Mar. 24, 2011

Related U.S. Application Data

(62) Division of application No. 11/667,100, filed as application No. PCT/FI2005/000470 on Nov. 30, 2005, now Pat. No. 7,863,311.

(60) Provisional application No. 60/625,129, filed on Nov. 5, 2004.

(30) Foreign Application Priority Data

Nov. 5, 2004  (FI) .................................. 20041425

(51) Int. Cl.
  *A01N 43/42* (2006.01)
  *A01N 43/78* (2006.01)
  *A01N 43/50* (2006.01)

(52) U.S. Cl. ......... 514/396; 514/307; 514/312; 514/365

(58) Field of Classification Search .................. 514/396
See application file for complete search history.

(56) References Cited

U.S. PATENT DOCUMENTS

| | | |
|---|---|---|
| 4,670,455 A | 6/1987 | Virtanen et al. |
| 5,446,070 A | 8/1995 | Mantelle |
| 5,464,628 A | 11/1995 | Jalonen et al. |
| 5,527,832 A | 6/1996 | Chi et al. |
| 5,925,344 A | 7/1999 | Ythier et al. |
| 6,562,363 B1 | 5/2003 | Mantelle et al. |
| 7,001,609 B1 * | 2/2006 | Matson et al. ................ 424/434 |
| 2004/0081699 A1 | 4/2004 | Rademacher et al. |

FOREIGN PATENT DOCUMENTS

| | | |
|---|---|---|
| EP | 1215024 A2 | 6/2002 |
| EP | 2004052347 A1 * | 6/2004 |
| WO | WO 00/19987 A | 4/2000 |
| WO | WO 02/11768 | 2/2002 |
| WO | WO 2004/052347 A | 6/2004 |

OTHER PUBLICATIONS

Pharmaceutical Encyclopedia, retrieved Jul. 11, 2008 [online], retrieved from: http://pharmapedia.blogspot.com/2008/02/3-theory-of-semisolid-dosage-forms.html, 3.2 Rheological Properties, printed pp. 1-7.
Dialog(R)File 351:Derwent WPI 0014319489: WPI Acc No. 2004-506956 English Abstract of WO 2004/052347.
International Search Report dated Feb. 6, 2006, for International Application No. PCT/FI2005/000470.
Malone J.H. et al., "A comparison of the efficacy of detomidine by sublingual and intramuscular administration in ponies," J. Vet. Anaesth., (1993), 20, 73-77.
Ramsay, E. C. et al., "Serum concentrations and effects of detomidine delivered orally to horses in three different mediums," Veterinary Anaesthesia and Analgesia, (2002), 29(4), 219-222.
Written Opinion dated Feb. 16, 2006, for International Application No. PCT/FI2005/000470.

* cited by examiner

*Primary Examiner* — Shengjun Wang
*Assistant Examiner* — Timothy E Betton
(74) *Attorney, Agent, or Firm* — Finnegan, Henderson, Farabow, Garrett & Dunner, LLP

(57) ABSTRACT

The present invention relates to a veterinary composition in a semisolid form adapted for transmucosal administration for providing sedation and analgesia in large animals such as horses and cattle. The semisolid transmucosal composition of the invention comprises detomidine or a pharmaceutically acceptable salt thereof as an active ingredient. The composition provides a rapid onset of action while having low irritation potential in the oral mucosa.

12 Claims, No Drawings

TRANSMUCOSAL VETERINARY COMPOSITION COMPRISING DETOMIDINE

This is a division of application Ser. No. 11/667,100, filed Jul. 19, 2007, now U.S. Pat. No. 7,863,311, which is a national stage application under §371 of International Patent Application No. PCT/FI2005/000470, filed on Nov. 3, 2005, issuance pending, and claims the benefit of U.S. Provisional Application No. 60/625,129, filed Nov. 5, 2004, and further claims priority to Finish Patent Application No. 20041425, filed on Nov. 5, 2004, all of which are incorporated herein by reference.

FIELD OF THE INVENTION

The present invention relates to methods and pharmaceutical compositions that are administered to animals, particularly for providing sedation, analgesia, restraint and anxiolytic effect in large animals such as horses and cattle.

BACKGROUND OF THE INVENTION

Detomidine which is 4-[(2,3-dimethylbenzyl)]imidazole of formula I

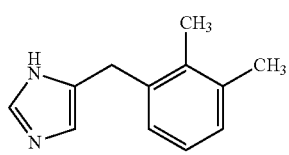

is a well known pharmaceutical agent currently used as its hydrochloride salt in veterinary use. Detomidine injectable solution (Domosedan®, Dormosedan®) is used for sedation and analgesia of horses and cattle during various examinations and treatments. Detomidine and its preparation are described in U.S. Pat. Nos. 4,443,466 and 4,584,383.

Administration of detomidine hydrochloride by injection provides rapid and reliable sedation in large animals, but the dosage form has to be given by a skilled animal care provider such as a veterinarian. Moreover, some large animals are "needle shy" which can make the administration by injection difficult. Therefore, other means for administering detomidine have been attempted.

Transmucosal administration by "squirting" detomidine injectable solution sublingually has been described (Malone, J. H. and Clarke K. W., J. Vet. Anaest., 20, Dec. 1993, 73-77). Useful sedation was achieved at the dose of 40 µg/kg by this method, but the rate at which the sedation developed (45 minutes for maximal effects) was substantially slower than after intramuscular injection.

In another study, detomidine injectable solution was delivered from a plastic syringe into the buccal or oral cavity of the horse as such or mixed with different food mediums such as apple sauce and gum mixture or molasses (Ramsay, E. C. et al, Veterinary Anaesthesia an Analgesia, 2002, 29, 219-222). The dose of 60 µg/kg was needed to produce adequate level of sedation, which produced profound head droop in horses in approximately 45 minutes.

Finally, transmucosal adhesive patches for veterinary use have been described in the International Patent Publication WO 00/19987 detomidine being mentioned as one of the suitable active agents. However, the present applicant has found that such transmucosal patch dosage forms of detomidine cause substantial, unacceptable local irritation if applied to oral mucosa of large animals such as horse. This irritation is most likely caused by the active agent detomidine itself and therefore it was found to be a major obstacle for the therapeutic administration of detomidine via transmucosal patch formulations.

Hence, there is still a need for improved products for the administration of detomidine in large animals such as horses and cattle, such products providing rapid onset of action, easy administration and low irritation potential.

SUMMARY OF THE INVENTION

The present invention relates to a pharmaceutical composition in a semisolid form adapted for transmucosal administration for providing sedation, analgesia, restraint and anxiolytic effect in animals, comprising detomidine or a pharmaceutically acceptable salt thereof as an active ingredient. In particular, the composition is in the form of transmucosal gel or emulsion.

It has been unexpectedly found that a semisolid composition of the invention, when applied on the oral mucosa of large animals such as horse, can provide a rapid onset of action comparable to intramuscular injection while having low irritation potential in the oral mucosa even after repeated dosing. The composition provides also longer duration of action than intravenous or intramuscular injections. Thus, the present invention provides a significant improvement over existing methods of administering detomidine to large animals such as horse and cattle.

Thus, according to one embodiment of the invention, the present invention provides a pharmaceutical veterinary composition in a semisolid form adapted for transmucosal administration comprising detomidine or a pharmaceutically acceptable salt thereof as an active ingredient.

According to another embodiment of the invention, the present invention provides a pharmaceutical veterinary composition in the form of a transmucosal gel or emulsion, comprising detomidine or a pharmaceutically acceptable salt thereof as an active ingredient.

According to one particularly preferred embodiment of the invention, the present invention provides a pharmaceutical veterinary composition in the form of a transmucosal gel, comprising detomidine or a pharmaceutically acceptable salt thereof as an active ingredient.

According to another embodiment of the invention, the present invention provides a veterinary kit comprising a) a composition in a semisolid form adapted for transmucosal administration comprising detomidine or a pharmaceutically acceptable salt thereof as an active ingredient, b) a package for containing said composition, and c) instructions for administering said composition on the mucosa, particularly oral mucosa, of an animal.

According to another embodiment of the invention, the present invention provides a veterinary kit comprising a) a composition in the form of a transmucosal gel or emulsion, comprising detomidine or a pharmaceutically acceptable salt thereof as an active ingredient, b) a package for containing said composition, and c) instructions for administering said composition on the mucosa, particularly oral mucosa, of an animal.

According to one particularly preferred embodiment of the invention, the present invention provides a veterinary kit comprising a) a composition in the form of a transmucosal gel, comprising detomidine or a pharmaceutically acceptable salt thereof as an active ingredient, b) a package for containing said composition, and c) instructions for administering said composition on the mucosa, particularly oral mucosa, of an animal.

According to another embodiment of the invention, the present invention provides a method of veterinary sedation comprising applying effective amount of a composition in a semisolid form adapted for transmucosal administration comprising detomidine or a pharmaceutically acceptable salt thereof as an active ingredient, on the mucosa, particularly oral mucosa, of an animal.

According to still another embodiment of the invention, the present invention provides the use of a composition in a semisolid form adapted for transmucosal administration comprising detomidine or a pharmaceutically acceptable salt thereof as an active ingredient, in the manufacture of a medicament for administration on the mucosa, particularly oral mucosa, of an animal.

DETAILED DESCRIPTION OF THE INVENTION

The present invention relates to a pharmaceutical veterinary composition in the semisolid form adapted for transmucosal administration, comprising detomidine or a pharmaceutically acceptable salt thereof as an active ingredient. The term "semisolid" mean here the mechano-physical state that is flowable under moderate stress. Preferably, the composition is easily syringable, meaning that it can readily be dispensed from a conventional tube of the kind well known for topical formulations or from needleless syringe. The semisolid composition should be viscous enough for being able to remain in the mouth of the animal, however the viscosity should not be so high that the composition could be swallowed. Preferably, the semisolid material should have a viscosity between about from about 500 to about 200,000 mPas, preferably from about 1,000 to about 100,000 mPas, more preferably from about 5,000 to about 50,000 mPas, for example from about 8,000 to about 30,000 mPas.

The semisolid composition of the present invention has a spreadable consistency upon administration. Thus, the present composition differs from earlier attempts in that it is not in the form of a patch, matrix, film or wafer, which dosage forms have a drawback of potential irritation.

The composition of the invention can be applied on any suitable mucosa of an animal including oral, nasal, vaginal and rectal mucosa. In particular, the composition of the invention is applied on the oral mucosa of an animal, e.g. buccal, lingual, sublingual or gingival mucosa. Preferably, it is applied sublingually from where detomidine is adsorbed through the mucous membranes of the oral cavity into the circulation and induces the desired pharmacological effect. The transmucosal, e.g. sublingual, route eliminates the pain caused by the needle penetrating the skin and is a particularly feasible route when the animal, e.g. a horse, for some reason can not be injected (needle shy patients). The composition of the invention is suitably applied sublingually in a small volume using a suitable applicator such as a syringe or the like. The composition remains in its application place and is not readily swallowed. It is especially useful for providing restraint, sedation, analgesia and/or anxiolytic effect in large animals, particularly in horses, ponies and cattle, during various examinations, treatments and transportations. The administration of the semisolid dosage is easy and can be performed by the animal owner or handler who is not skilled in parenteral drug administration. The onset of the effect, e.g. sedation, is rapid, and generally starts in horse within 30 minutes, preferably within 25 minutes, more preferably within 20 minutes, from the time application. The duration of the sedative effect is preferably from about 180 to about 300 minutes.

The amount of detomidine or a pharmaceutically acceptable salt thereof in the composition is selected such as to provide the desired pharmacological effect. The actual amount of the drug administered may depend on numerous factors, such as the species, age and weight of the subject to be treated, the desired duration of use and the effect to be achieved. It should be noted that the present invention is intended to encompass all of the potential uses of the present composition which derive from the activity of detomidine as an adrenergic alpha-2-receptor agonist, e.g. its use as a sedative, anxiolytic, analgesic, and the like. Typically, detomidine or a pharmaceutically acceptable salt thereof, preferably hydrochloride salt, is administered to a subject in doses ranging from about 1 to about 200 µg/kg, more typically from about 10 to about 100 µg/kg, preferably from about 20 to about 80 µg/kg.

The concentration of detomidine or a pharmaceutically acceptable salt thereof is generally within the range of about 0.1 to about 5% (w/w), preferably from about 0.2 to about 2% (w/w), suitably from about 0.5 to about 1% (w/w), per weight of the composition.

Pharmaceutically acceptable salts of detomidine can be prepared by known methods. Suitable salts include acid addition salts formed, for example, with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid and the like. Detomidine hydrochloride is the preferred salt.

The semisolid composition of the invention may be for example a gel, cream, ointment or paste. Preferably the composition of the invention is in the form of a gel or emulsion. Gel form is particularly preferred.

Semisolid dosage forms of the invention can be prepared by methods well known in the art. They can be prepared by combining the drug substance with conventional pharmaceutical diluents and carriers commonly used in semisolid formulations.

Emulsions of the present invention consist of an aqueous phase and an oil phase. The compositions may take the form of a water-in-oil (W/O) emulsion or, preferably, an oil-in-water (O/W) emulsion. Suitably, the emulsions comprise from about 50 to about 95% (w/w), preferably from about 70 to about 90% (w/w), per weight of the composition, of water. The oil phase of the emulsion may comprise, for example, petrolatum, liquid paraffin, vegetable oils including peanut oil or castor oil, waxes, caprylic/capric triglyceride, fatty alcohols such as stearyl alcohol or cetyl alcohol, and the like. Suitably, the oil phase takes from about 1 to about 30% (w/w), preferably from about 3 to about 20% (w/w), per weight of the composition.

The emulsions may further comprise various additives such as emulsifiers, buffers, wetting agents, stabilizers, preservatives, thickening agents and the like.

It may be desired to employ an emulsifier in order to form a stable emulsion. Suitable emulsifiers are, for example, anionic, cationic or non-ionic emulsifiers. Typical emulsifiers include polyoxyethylated fatty esters, polyoxyethylated fatty alcohol ethers, glyceryl esters, sorbitan esters, polyethylene glycol stearates and polyoxyethylene derivatives of sorbitan esters. Specific examples include polyethylene glycol 100 stearate (PEG-100 stearate), glyceryl monostearate, glyceryl monoleate, stearic acid, polyoxyethylene cetyl ether, polyoxyethylene cetostearyl ether, polyoxyethylene stearyl ether, sorbitan monostearate, and polysorbate 60. Suitably, emulsifiers are employed from about 0.5 to about 10% (w/w), preferably from about 1 to about 3% (w/w), per weight of the composition.

Emulsion may also comprise thickening agents such as soft paraffin, cellulose derivatives, carbomers, cetearyl alcohol, propylene glycol, butylene glycol, polyethylene glycols, hydrogenated lanolin, beeswax, and the like.

The drug substance is preferably included in the aqueous phase in the emulsions of the invention.

Gel, as referred to herein, is a single phase semisolid system consisting of organic macromolecules (gelling agent) uniformly distributed throughout a liquid in such a manner that no apparent boundaries exists between the dispersed macromolecules and the liquid. A veterinary transmucosal composition in the form of a gel has been found to be a particularly suitable embodiment of the invention.

Gel structure is obtainable by using a suitable gelling agent. The amount of gelling agent is selected such that the resulting gel has the desired rheological properties. The gel according to the invention is preferably an aqueous gel (hydrogel), wherein the liquid solvent comprises water. However, the aqueous gel formulation may also comprise suitable water-miscible co-solvents. The active ingredient is uniformly dissolved or dispersed in the gel composition.

Preferably, the transmucosal gel formulation according to the invention comprises detomidine or a pharmaceutically acceptable salt thereof, a gelling agent, a transmucosal penetration enhancer, water-miscible organic co-solvent and water.

The gelling agent may be any suitable hydrophilic gel forming polymer. Preferably, the gelling agent is selected from cellulose derivatives, polyacrylic acids and polyoxyethylene/polyoxypropylene copolymers. Cellulose derivatives and polyacrylic acids are particularly preferred gelling agents.

Suitable cellulose derivatives for use as gelling agents include cellulose ethers such as hydroxypropyl cellulose, hydroxyethyl cellulose, hydroxyethyl methylcellulose, methylcellulose, hydroxypropyl methylcellulose, hydroxypropyl ethylcellulose, hydroxycellulose and the like. Preferred cellulose ethers include hydroxypropyl cellulose and hydroxyethyl cellulose.

Suitable polyacrylic acids for use as gelling agents include carbomers (also called carboxyvinyl polymers). Carbomers are polyalkenyl polyether cross-linked polymers acrylic acids, typically polyallyl sucrose or polyallyl pentaerythritol cross-linked polymers of acrylic acid. They are available e.g. under the tradename Carbopol in various grades. Aqueous carbomer dispersions are acidic due to free carboxyl groups of the carbomer polymer. Neutralization of the aqueous dispersions of carbomer polymers causes spontaneous thickening through formation of water-soluble salts of polymer resins.

The gel should be viscous enough for being able to remain in the mouth of the animal, however the viscosity should not be so high that the gel could be swallowed by the animal.

The gelling agents are generally used in an amount suitable to provide a gel with a viscosity from about 500 to about 200,000 mPas, preferably from about 1,000 to about 100,000 mPas, more preferably from about 5,000 to about 50,000 as, for example from about 8,000 to about 30,000 mPas, measured on a Brookfield Digital Viscometer DV-II, LV-4 (cylindrical spindle), spindlefactor 64, 12 rpm, 25° C.

Such suitable viscosity may be obtained by adjusting the amount of gelling agent and/or by adjusting the pH of the composition. This is especially relevant where the gelling agent is a polyacrylic acid such as carbomer as its viscosity is dependent on the pH of the composition.

The amount of the gelling agent depends on the nature of the gelling agent and the desired viscosity. It is preferred that the gel has a spreadable consistency which allows easy sublingual administration of a small volume of the gel from a syringe or the like. Preferably, the gel composition of the invention is free of bioadhesive components, such as elastomers or the like. Moreover, the gel composition of the invention is preferably not a film-forming type gel composition.

Generally the amount of the gelling agent in the composition of the invention is from about 0.3 to about 40% (w/w), per weight of the composition. In case where the gelling agent is a cellulose derivative, the amount of the gelling agent is typically from about 0.5 to about 40% (w/w), more preferably from about 1 to about 30% (w/w), per weight of the composition. In case where the gelling agent is a polyacrylic acid such as carbomer, the amount of the gelling agent is typically from about 0.3 to about 5.0% (w/w), more preferably from about 0.5 to about 3.0% (w/w), per weight of the composition.

In case where the gelling agent is hydroxypropyl cellulose, it is suitably used in an amount ranging from about 5 to about 40% (w/w), preferably from about 10 to about 25% (w/w), per weight of the composition.

The pH of the composition is suitably within the range of from about 4 to about 8, preferably from about 5 to about 7, more preferably from about 5.5 to about 6.5, particularly between about 5.8 and 6.2. The pH may be adjusted with a suitable basic compound, such as sodium hydroxide, fatty amine or a tertiary amine, or with an acidic compound, such as hydrochloric acid. A gelling agent is typically a slightly acidic material.

Transmucosal penetration enhancers are agents capable of increasing the rate at which the drug permeates through the mucosal membranes and enters the bloodstream. Suitable transmucosal penetration enhancers include for example surfactants, e.g. anionic surfactants such as salts of fatty acids of 5 to 30 carbon atoms, e.g. sodium lauryl sulphate and other sulphate salts of fatty acids, cationic surfactants such as alkylamines of 8 to 22 carbon atoms, e.g. oleylamine, and non-ionic surfactants such as polysorbates and poloxamers; aliphatic monohydric alcohols of 8 to 22 carbon atoms such as decanol, lauryl alcohol, myristyl alcohol, palmityl alcohol, linolenyl alcohol and oleyl alcohol; fatty acids of 5 to 30 carbon atoms such as oleic acid, stearic acid, linoleic acid, palmitic acid, myristic acid, lauric acid and capric acid and their esters such as ethyl caprylate, isopropyl myristate, methyl laurate, hexamethylene palmitate, glyceryl monolaurate, polypropylene glycol monolaurate and polyethylene glycol monolaurate; diethyleneglycol monoethyl ether (Transcutol); menthol and other essential oils; salicylic acid and its derivatives; alkyl methyl sulfoxides such as decyl methyl sulfoxide and dimethyl sulfoxide (DMSO); 1-substituted azacycloalkan-2-ones such as 1-dodecylazacyclo-heptan-2-one sold under the trademark AZONE; amides such as octylamide, oleicamide, hexamethylene lauramide, lauric diethanolamide, polyethylene glycol 3-lauramide, N,N-diethyl-m-toluamide and crotamiton; and any other compounds compatible with detomidine and having transmucosal penetration enhancing activity. One or several of the above transmucosal penetration enhancers can be used. The amount of the transmucosal penetration enhancer in the composition is generally from about 0.1 to about 20% (w/w), preferably from about 0.2 to about 15% (w/w), more preferably from about 0.5 to about 10% (w/w) per weight of the composition, depending on the transmucosal permeation enhancer used.

Preferred transmucosal penetration enhancers are fatty acids of 5 to 30 carbon atoms, particularly isopropyl myristate; sulphate salts of 5 to 30 carbon fatty acids, particularly sodium lauryl sulphate; and DMSO. Sodium lauryl sulphate is particularly preferred.

In case the transmucosal penetration enhancer is sodium lauryl sulphate, it is used in an amount ranging from about 0.1 to about 5% (w/w), preferably from about 0.2 to about 3% (w/w), suitably from about 0.5 to about 2% (w/w), per weight of the composition.

Water-miscible organic co-solvents suitable for use in the gel compositions of present invention include polyalcohols or glycols such as propylene glycol, butylene glycol, ethylene glycol, preferably propylene glycol or $C_2$-$C_4$ alkanols such as ethanol, isopropanol, n-propanol or butanol; or combinations thereof. Preferred are non-volatile organic co-solvents, particularly propylene glycol. The amount of the water-miscible organic co-solvent in the composition is generally from about 5 to about 50% (w/w), preferably from about 10 to about 45% (w/w), more preferably from about 15 to about 40% (w/w), for example from about 20 to about 35% (w/w), per weight of the composition.

The amount of water in the gel composition is generally from about 15 to about 90% (w/w), preferably from about 20 to about 80% (w/w), more preferably from about 30 to about 75% (w/w), for example from about 40 to about 70% (w/w), per weight of the composition.

According to one preferred embodiment of the invention, the transmucosal gel formulation of the invention comprises, per weight of the composition, 0.1-5% (w/w) of detomidine or a pharmaceutically acceptable salt thereof; 0.3-40% (w/w) of a gelling agent; 0.2-15% (w/w) of a transmucosal penetration enhancer; 5-50% (w/w) of a water-miscible organic co-solvent; and 30-80% (w/w) of water.

The gel composition of the invention can optionally also include other excipients commonly used in the art, for example, preservatives and/or antioxidants such as benzyl alcohol, methyl and propyl parabens, butylhydroxytoluene or butylhydroxyanisole; sweeteners; colouring agents; flavouring agents; buffers; pH adjusting agents; and solubilizers such as glycerol and the like.

The composition of the invention is preferably given to a subject animal sublingually from a prefilled syringe in a volume ranging from about 1 to 10 ml, more preferably from about 2 to 5 ml, for example 3 ml.

The composition of the invention comprises preferably a colouring agent. For example, a coloured gel can be easily distinguished from saliva following the administration. If the gel product is discharged from the mouth of the animal the owner will be able to note the approximate loss of gel. The owner will also easily note any accidental dosing in case the product comes into contact with his skin.

Preferably, the composition of the invention consists essentially of non-food ingredients. The term "non-food ingredients" means here ingredients that are not conventionally used as food substance or nutrient for humans or animals.

The composition can be provided in the form of a veterinary kit that comprises composition of the invention, a package for containing said composition, and instructions for administering said composition on the oral mucosa of an animal. Preferably, said package is an applicator, e.g. a syringe capable of dosing fixed volumes of the composition of the invention. Syringe is preferably prepared form polymer material, such as HDPE. Suitably, the volume of the syringe ranges from about 1 to 20 ml, more preferably from about 2 to 10 ml. For example, composition of the invention can be packaged into 4 ml, 5 ml or 10 ml HDPE syringes.

The invention is her illustrated by the following examples, which are not meant to limit the scope of the invention.

EXAMPLES

Example 1

| Ingredient | % (w/w) |
| --- | --- |
| Detomidine HCl | 1.0 |
| Hydroxypropyl Cellulose | 20 |
| Propylene Glycol | 30 |
| DMSO | 5 |
| Sodium Hydroxide (1M) | 1.1 |
| Water | 42.9 |
| pH | 5.8-6.2 |

The gel formulation of Example 1 was prepared by dissolving the drug substance to water. To this mixture propylene glycol, dimethylsulphoxide and sodium hydroxide were added under stirring. Finally hydroxypropyl cellulose was added and the formulation was homogenized by stirring.

Example 2

| Ingredient | % (w/w) |
| --- | --- |
| Detomidine HCl | 0.75 |
| Hydroxyethyl Cellulose | 2.2 |
| Propylene Glycol | 30 |
| Sodium Lauryl Sulphate | 1 |
| Sodium Hydroxide (1M) | q.s. |
| Water | To 100 |
| pH | 5.8-6.2 |

The gel formulation of Example 2 was prepared by dissolving the drug substance to water. To this mixture propylene glycol and sodium lauryl sulphate were added under stilling. Finally hydroxyethyl cellulose was added and the formulation was homogenized by stirring after adjusting the pH by addition of sodium hydroxide.

Example 3

| Ingredient | % (w/w) |
| --- | --- |
| Detomidine HCl | 0.75 |
| Carbopol | 1.0 |
| Propylene Glycol | 30 |
| Isopropyl myristate | 1 |
| Sodium Hydroxide (1M) | q.s. |
| Water | To 100 |
| pH | 5.8-6.2 |

The gel formulation of Example 3 was prepared by dissolving the drug substance to water. To this mixture propylene glycol was added under stirring. Carbopol and isopropyl myristate were first mixed in a pestle and mortar and then added slowly into the solution under stirring. Finally the formulation was homogenized by stirring after adjusting the pH by addition of sodium hydroxide.

Example 4

| Ingredient | % |
|---|---|
| Detomidine HCl | 0.72 |
| Hydroxypropyl Cellulose | 15 |
| Propylene Glycol | 30 |
| Sodium Lauryl Sulphate | 1 |
| Sodium Methyl Paraben | 0.1 |
| Sodium Propyl Paraben | 0.1 |
| FD&C Blue No 1 | 0.003 |
| Sodium Hydroxide (5%)/HCl (8.5%) | q.s. |
| Water | 53.075 |
| pH | 6.0 |

The gel formulation of Example 4 was prepared by adding propylene glycol, parabens, sodium lauryl sulphate and water in a vessel. The mixture was stirred until it was miscible and homogenous. Drug substance and colouring agent were added under stirring. The mixture was warmed to 50° C. Hydroxypropyl cellulose was slowly added under stirring. The gel was cooled to room temperature under gentle stirring and pH of the composition was adjusted to 6.0 by dropwise addition of HCl solution. Clear blue gel was obtained after standing. Gel was packaged into 5 ml HDPE syringes.

Example 5

| Ingredient | % (w/w) |
|---|---|
| Detomidine HCl | 0.75 |
| Butylene glycol | 5.0 |
| Decyl oleate | 5.0 |
| Cetearyl alcohol | 3.6 |
| PEG-6 stearate | 2.0 |
| Glycol stearate | 1.0 |
| PEG-32 stearate | 1.0 |
| Sodium cetearyl sulphate | 0.4 |
| Water | To 100.0 |

The emulsion formulation of Example 5 is prepared by adding butylene glycol, decyl oleate, cetearyl alcohol, PEG-6 stearate, glycol stearate, PEG-32 stearate and sodium cetearyl sulphate in a vessel. The mixture is warmed to 80° C. and homogenized. Water (part) is added and the mixture is warmed to 100° C. under stirring. The mixture is cooled to 80° C. and the drug substance dissolved in the rest of water is added to the mixture. The mixture is homogenized under vacuum and cooled.

Example 6

| Ingredient | % (w/w) |
|---|---|
| Detomidine HCl | 0.75 |
| Caprylic/Capric triglyceride | 3.0 |
| Polydecene | 3.0 |
| Petrolatum | 3.0 |
| Glycerin | 2.6 |
| PEG-100 stearate | 1.5 |
| Glyceryl stearate | 1.5 |
| Cetearyl alcohol | 1.0 |
| Phenoxyethanol | 0.8 |
| Sodium carbomer | 0.3 |
| Water | To 100.0 |

The emulsion formulation of Example 6 is prepared by adding polydecene, petrolatum, cetearyl alcohol, glyceryl stearate, PEG-100 stearate and caprylic/capric triglyceride in a vessel. The mixture is warmed to 80° C. and homogenized. Glycerin, phenoxyethanol and the drug substance dissolved in a part of water are mixed and warmed to 75° C. and then added to the mixture under stirring. The mixture is cooled to 40° C. Sodium carbomer and the rest of water (20° C.) is mixed and homogenized in another vessel and then added to the mixture. pH is adjusted to 6 and the mixture is homogenized under vacuum and cooled.

The invention claimed is:

1. A veterinary pharmaceutical composition comprising an effective amount of a composition in the form of semisolid transmucosal for transmucosal administration gel for transmucosal administration comprising, per weight of the composition, from 0.1% to 5% (w/w) of detomidine or a pharmaceutically acceptable salt thereof; from 5% to 40% (w/w) of gelling agent which is hydroxypropyl cellulose; from 0.2% to 3% (w/w) of a transmucosal penetration enhancer which is sodium lauryl sulphate; from 5% to 50% (w/w) of propylene glycol; and from 30% to 75% (w/w) of water.

2. The veterinary pharmaceutical composition according to claim 1, wherein the composition comprises, per weight of the composition, from 0.2% to 2% (w/w) of detomidine or a pharmaceutically acceptable salt thereof.

3. The veterinary pharmaceutical composition according to claim 1, wherein the composition comprises, per weight of the composition, from 10% to 25% (w/w) of hydroxypropyl cellulose.

4. The veterinary pharmaceutical composition according to claim 1, wherein the composition comprises, per weight of the composition, from 0.5% to 2% (w/w) of sodium lauryl sulphate.

5. The veterinary pharmaceutical composition according to claim 1, wherein the composition comprises, per weight of the composition, from 10% to 45% (w/w) propylene glycol.

6. The veterinary pharmaceutical composition according to claim 1, wherein the composition comprises, per weight of the composition, from 40% to 70% (w/w) water.

7. The veterinary pharmaceutical composition according to claim 1, wherein the composition has a viscosity from 5,000 to 50,000 mPas.

8. The veterinary pharmaceutical composition according to claim 1, wherein the composition has a pH value ranging from 5 to 7.

9. The veterinary pharmaceutical composition according to claim 1, wherein the composition has a viscosity from 500 to 200,000 mPas.

10. The veterinary pharmaceutical composition according to claim 1, wherein the composition has a viscosity from 1,000 to 100,000 mPas.

11. The veterinary pharmaceutical composition according to claim 1, wherein the composition has a viscosity from 8,000 to 30,000 mPas.

12. The veterinary pharmaceutical composition according to claim 1, wherein the composition comprises from 0.2% to 2% (w/w) of detomidine or a pharmaceutically acceptable salt thereof, from 10% to 25% (w/w) of hydroxypropyl cellulose, from 0.5% to 2% (w/w) of sodium lauryl sulphate, from 10% to 45% (w/w) propylene glycol, and from 40% to 70% (w/w) water.

* * * * *

UNITED STATES PATENT AND TRADEMARK OFFICE
CERTIFICATE OF CORRECTION

| | |
|---|---|
| PATENT NO. | : 8,309,591 B2 |
| APPLICATION NO. | : 12/953691 |
| DATED | : November 13, 2012 |
| INVENTOR(S) | : Mirja Huhtinen et al. |

It is certified that error appears in the above-identified patent and that said Letters Patent is hereby corrected as shown below:

On the title page Item (62), line 2:

"Nov. 30,"

should read

--Nov. 3,--.

Signed and Sealed this
Twelfth Day of March, 2013

Teresa Stanek Rea
*Acting Director of the United States Patent and Trademark Office*